(12) United States Patent
Che et al.

(10) Patent No.: US 7,695,758 B2
(45) Date of Patent: *Apr. 13, 2010

(54) ORGANOMETALLIC LIGHT-EMITTING MATERIAL

(76) Inventors: Chi-Ming Che, Flat 5, 5/F, Block A, Parkway Court, 4 Park Road, Hong Kong (CN); Wei Lu, 7/F, Room B, 41 Western Street, Hong Kong (CN); Michael Chi-Wang Chan, 9B Fairview Court, 75 Pokfulam Road, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 11/681,412

(22) Filed: Mar. 2, 2007

(65) Prior Publication Data

US 2007/0148334 A1 Jun. 28, 2007

Related U.S. Application Data

(63) Continuation of application No. 11/468,757, filed on Aug. 30, 2006, which is a continuation of application No. 11/401,537, filed on Apr. 10, 2006, which is a continuation of application No. 10/094,384, filed on Mar. 8, 2002, now Pat. No. 7,026,480.

(60) Provisional application No. 60/274,142, filed on Mar. 8, 2001.

(51) Int. Cl.
*B05D 5/06* (2006.01)

(52) U.S. Cl. ............ 427/66; 427/70; 313/504; 428/917; 445/24

(58) Field of Classification Search ............ 427/66, 427/70; 313/504; 428/917; 445/24
See application file for complete search history.

(56) References Cited

U.S. PATENT DOCUMENTS 5,698,048 A 12/1997 Friend et al.

(Continued)

FOREIGN PATENT DOCUMENTS

WO WO 00/57676 9/2000

(Continued)

OTHER PUBLICATIONS

Office Action, mailed May 19, 2003, for related U.S. Appl. No. 10/094,384.

(Continued)

*Primary Examiner*—Timothy H Meeks
*Assistant Examiner*—Jimmy Lin
(74) *Attorney, Agent, or Firm*—McDonnell Boehnen Hulbert & Berghoff LLP

(57) ABSTRACT

Disclosed herein are novel light-emitting materials of Formula I and II below. These new complexes are synthesized and found to be sufficiently stable to allow sublimation and vacuum deposition. These new emitters are electrophosphorescent and can be used in organic light-emitting devices (OLEDs) for device elements capable of emitting light of color ranging from orange to red with high-efficiency and high-brightness.

The heterostructure of OLEDs in present invention.

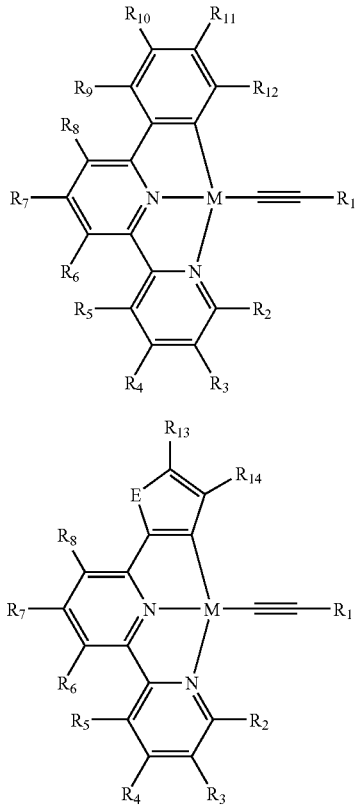

wherein E=Group 16 elements (including sulphur); M=Group 10 metal (including platinum); $R_1$-$R_{14}$ are each independently selected from the group consisting of hydrogen; halogen; alkyl; substituted alkyl; aryl; substituted aryl, with substituents selected from the group consisting of halogen, lower alkyl and recognized donor and acceptor groups. $R_1$ can also be selected from $(C\equiv C)_n R_{15}$, where $(C\equiv C)$ represents a carbon-carbon triple bond (acetylide group), n is selected from 1 to 10, and $R_{15}$ is selected from alkyl, aryl, substituted aryl, and tri(alkyl)silyl.

17 Claims, 10 Drawing Sheets

U.S. PATENT DOCUMENTS

| | | | |
|---|---|---|---|
| 6,048,630 A | 4/2000 | Burrows et al. | |
| 6,120,586 A | 9/2000 | Harada et al. | |
| 6,150,545 A | 11/2000 | Harada et al. | |
| 6,252,028 B1 | 6/2001 | Fehn et al. | |
| 6,447,934 B1* | 9/2002 | Suzuki et al. | 428/690 |
| 6,458,475 B1* | 10/2002 | Adachi et al. | 428/690 |
| 7,026,480 B2 | 4/2006 | Che et al. | |
| 2001/0028962 A1* | 10/2001 | Hirai | 428/690 |
| 2001/0050531 A1* | 12/2001 | Ikeda | 313/498 |
| 2002/0068192 A1* | 6/2002 | Moriyama et al. | 428/690 |
| 2002/0179885 A1* | 12/2002 | Che et al. | 252/301.16 |
| 2004/0091738 A1 | 5/2004 | Psai et al. | |
| 2006/0094875 A1 | 5/2006 | Itoh et al. | |
| 2006/0175605 A1 | 8/2006 | Che et al. | |
| 2007/0104978 A1 | 5/2007 | Che et al. | |

FOREIGN PATENT DOCUMENTS

WO    WO 01/41512 A1    6/2001

OTHER PUBLICATIONS

Amendment, mailed Aug. 18, 2003, for related U.S. Appl. No. 10/094,384.
Final Office action, mailed Sep. 30, 2003, for related U.S. Appl. No. 10/094,384.
Response to Final Office action and Notice of Appeal, mailed Dec. 30, 2003, for related U.S. Appl. No. 10/094,384.
Advisory Action, mailed Feb. 18, 2004, for related U.S. Appl. No. 10/094,384.
Response to Advisory Action, mailed May 14, 2004, for related application no. 10/094,384.
Office Action, mailed May 25, 2004, for related U.S. Appl. No. 10/094,384.
Amendment, mailed Jul. 8, 2004, for related U.S. Appl. No. 10/094,384.
*Ex Parte* Quayle Amendment, mailed Sep. 23, 2004, for related U.S. Appl. No. 10/094,384.
Notice of Allowance, mailed Oct. 28, 2004, for related U.S. Appl. No. 10/094,384.
Office Action, mailed Jul. 17, 2006, for related U.S. Appl. No. 11/401,537.
Response, mailed Jan. 18, 2007, for related U.S. Appl. No. 11/401,537.
Final Office Action, mailed Mar. 7, 2007, for related U.S. Appl. No. 11/401,537.
Response, mailed Aug. 7, 2007, for related U.S. Appl. No. 11/401,537.
Office Action, mailed Sep. 13, 2007, for related U.S. Appl. No. 11/401,537.
Siu-Wai Lai, et al, Inorganic Chem 38(18) pp. 4046-4055, 1999.
Siu-Wai Lai, Organometallics pp. 3327-3336, 1999.
Raffaello Romeo, Inorganica Chimica Acta, vol. 265, Issues 1-2, Nov. 15, 1997, pp. 225-233.
Yurngdong Jahng, Inorganica Chimica Acta, vol. 267, Issue 2, Jan. 10, 1998, pp. 265-270.
Chin Wing Chan, JACS, pp. 11245-11253, 1993.
Minghetti, Inorganic Chemistry 29(26) pp. 5137-5138 (1990).
Malcolm H. Chisholm Inorg. CHem 16(9), 1977, pp. 2177-2182.
R. A. Bell, Inorg Chem 16(3), 1977, pp. 677-686.
Robert A. Bell Inorg Chem 16(3), 1977, pp. 687-697.
C. W. Tang and S. A. VanSlyke, "Organic electroluminescent diodes", *Appl. Phys. Lett. 51* (12), Sep. 21, 1987, pp. 913-915.
David E. Mentley, "The Market Potential for Organic Light-Emitting Diode Displays", *Commercial Report*, Stanford Resources, 5 pages.
M. A. Baldo, D. F. O'Brien, Y. You, A. Shoustikov, S. Sibley, M. E. Thompson & S. R. Forrest, "Highly efficient phosphorescent emission from organic electroluminescent devices", *Nature*, vol. 395, Sep. 10, 1998, pp. 151-154.
Yuguang Ma, Houyu Zhang, Jiacong Shen, Chiming Che, "Electroluminescence from triplet metal-ligand charge-transfer excited state of transition metal complexes", *Synthetic Metals 94* (1998), pp. 245-248.
Chihaya Adachi, Marc A. Baldo and Stephen R. Forrest, "High-efficiency organic electrophosphorescent devices with tris (2-phenylpyridine)iridium doped into electron-transporting materials", *Applied Physics Letters*, Vol. 77, No. 6, Aug. 7, 2000, pp. 904-906.
Siu-Wai Lai, Michael Chi-Wang Chan, Tsr-Chun Cheung, Shie-Ming Peng and Chi-Ming Che, "Probing $d^8$-$d^8$ Interactions in Luminescent Mono- and Binuclear Cyclometalated Platinum(II) Complexes of 6-Phenyl-2,2'- bipyridines", *Inorg. Chem.* 1999,38, pp. 4046-4055.
Tsz-Chun Cheung, Kung-Kai Cheung, Shie-Ming Peng and Chi-Ming Che, "Photoluminescent cyclometallated diplatinum(II,II) complexes: photophysical properties and crystal structures of [PtL(PPh$_3$)ClO$_4$ and [Pt$_2$L$_2$(p-dppm)] [ClO$_4$]$_2$ (HL+ 6-phenyl-2,2'-bipyridine, dppm = Ph$_2$PCH$_2$PPh2)", *J. Chem. Soc., Dalton Trans.* 1996, p. 1645-1651.

Siu-Wai Lai, Michael Chi-Wang Chan, Kung-Kai Cheung and Chi-Ming Che, "Carbene and Isocyanide Ligation at Luminescent Cyclometalated 6-Phenyl-2,2'-bipyridyl Platinum(II) Complexes: Structural and Spectroscopic Studies", *Organometallics 1999*, 18, pp. 3327-3336.

John H. K. Yip, Suwarno and Jagadese J. Vittal, "Syntheses and Electronic Spectroscopy of [PtL(L1)] [ClO,] Complexes (HI, = 6-Phenyl-2,2'-bipyridine; L' = Pyridine, 4-Aminopyridine, 2-Aminopyridine, and 2,6- Diaminopyridine)", *Inorgan. Chem. 2000*, 39, pp. 3537-3543.

Francesco Neve and Alessandra Crispini, Sebastiano Campagna, "Anisometric Cyclometalated Palladium(II) and Platinum(II) Complexes. Structural and Photophysical Studies", *Inorg. Chem. 1997*,36, pp. 6150-6156.

Fritz Krohke. "The Specific Synthesis of Pyridines and Oligopyridines", *Synthesis*, Jan. 1976, pp. 1-24.

S. Takahashi, Y. Kuroyama, K. Sonogashira and N. Hagihara, , "A Convenient synthesis of Ethynylarenes and Diethynylarenes", Communications, *Synthesis*, Aug. 1980, pp. 627-630.

Edwin C. Constable, Roland P. G. Henney, Paul R. Raithby and Lynn R. Sousa, "Cyclometallation Reactions of 6-(2-Thienyl)-2,2'-bipyridine with $d^8$ Transition Metal Ions", *J. Chem. Soc. Dalton Trans*. 1992, pp. 225 1-2258.

Edwin C. Constable, Roland P. G. Henney and Troy A. Leese, Derek A. Tocher, "Cyclometallation Reactions of 6-Phenyl-2,2'-bipyridine; a Potential C,N,N-DonorAnalogue of 2,2':6',2"-Terpyridine, Crystal and Molecular Structure of Dichlorobis(6-phenyl-2-2'-bipyridine)ruthenium(II)", J. Chem. Soc. Dalton Trans. 1990, pp. 443-449.

Wei Lu, Boa-Xiu Mi, Michael C. W. Chan, Zheng Hui, Nianyong Zhu, Shuit-Tong Lee and Chi-Ming Che, "[C∧N∧N)Pt(C≡C)$_n$R] (HC∧N∧N = 6-aryl-2,2'-bipyridine, $n$ = 1–4, R = aryl, SiMe$_3$) as a new class of light-emitting materials and their applications in electrophosphorescent devices", *Chemical Communications*, DOI: 10.1039/b108793b, 4 pages.

Vladimir V. Grushin, Norman Herron, Daniel D. LeCloux, William J. Marshall, Viacheslav A. Petrov and Ying Wang, "New, efficient electroluminescent materials based on organometallic Ir complexes", *Chem, Commun*., 2001, pp. 1494-1495.

Hong Zhi Xie, Man Wah Liu, Oi Yan Wang, Xiao Hong Zhang, Chun Sing Lee, Liang Sun Hung, Shuit Tong Lee, Pang Fei Teng, Hoi Lun Kwong, Hui Zheng and Chi Min Che, "Reduction of Self-Quenching Effect in Organic Electrophosphorescence Emitting Devices via the Use of Sterically Hindered Spacers in Phosphorescence Molecules", *Advanced Materials* 2001, 13, No. 16, Aug. 16, pp. 1245-1248.

Sergey Lamansky, Peter Djurovich, Drew Murphy, Feras Abdel-Razzaq, Hae-Eun Lee, Chihaya Adachi, Paul E. Burrows, Stephen R. Forrest and Mark E. Thompson, "Highly Phosphorescent Bis-Cyclometalated Iridium Complexes: Synthesis, Photophysical Characterization, and Use in Organic Light Emitting Diodes", *J. Am. Chem* Soc. 2001 vol. 123, No. 18, pp. 4304-4312.

Chihaya Adachi, Marc A. Baldo, Mark E. Thompson and Stephen R. Forrest, "Nearly 100% internal phosphorescence efficiency in an organic light emitting device", *Journal of Applied Physics*, vol. 90, No. 10, Nov. 15, 2001, pp. 5048-5051.

Chihaya Adachi, Raymond C. Kwong, Peter Djurovich, Vadim Adamovich, Marc A. Baldo, Mark E. Thompson and Stephen R. Forrest, "Endothermic energy transfer: A mechanism for generating very efficient high-energy phosphorescent emission in organic materials", *Applied Physics Letters*, Vol. 79, No. 13, Sept. 24, 2001, pp. 2082-2084.

Chihaya Adachi, Marc A. Baldo and Stephen R. Forrest, "High-efficiency red electrophosphorescence devices", *Applied Physics Letters*, vol. 78, No. 11, Mar. 12, 2001, pp. 1622-1624.

O'Brien et al., "Improved energy transfer in electrophosphorescent devices," Appl. Phys. Lett., 74(3):442-444 (Jan. 18, 1999).

Bunten, et al., "Synthesis, Optical Absorption, Fluorescence, Quantum Efficiency, and Electrical Conductivity Studies of Pyridine/Pyridinium Dialkynyl Organic and Pt(II)-σ-Acetylide Monomers and Polymers," Macromolecules, 29 (8):2885-2893 (Mar. 2001).

Wong et al., "Synthesis, Redox and Optical Properties of Low-Bandgap Platinum(II) Polyynes with 9-Dicyanomethylene-Substituted Fluorene Acceptors", Macromol. Rapid Commun., 22:461-465 (Mar. 2001).

Back et al., Bis-ortho-chelated Diaminoaryl Platinum Compounds with σ-Acetylene Substituents, Investigations into Their Stability and Subsequent Construction of Multimetallic Systems. The Crystal Structure of [(μ2-[η2-NCN)Pt(η1-CO)C—CSiMe3])Co2(CO)6] (NCN= 2,6-Bis[(dimethylamino)methyl]phenyl), Organometallics,19(17):3296-3304 (2000).

Back et al., "Mixed Metal Acetylides: the PtII Aryl Acetylide "[Ptc6H2(CH2NMe2)2- 2,6-(C—C)-4]" as a Connective Fragment," European Journal of Inorganic Chemistry, 20(7):1457-1464 (2000).

* cited by examiner

Figure 1. General heterostructure of OLEDs.
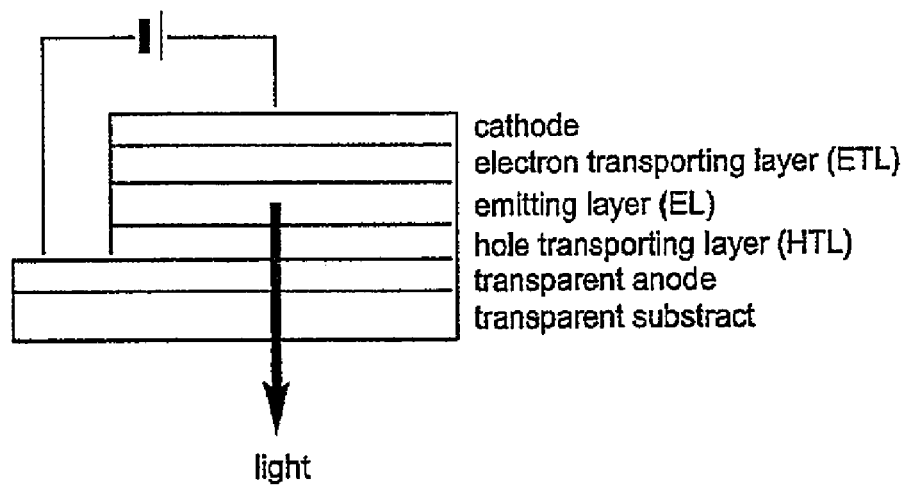

Figure 2. TGA curve of complex 2.
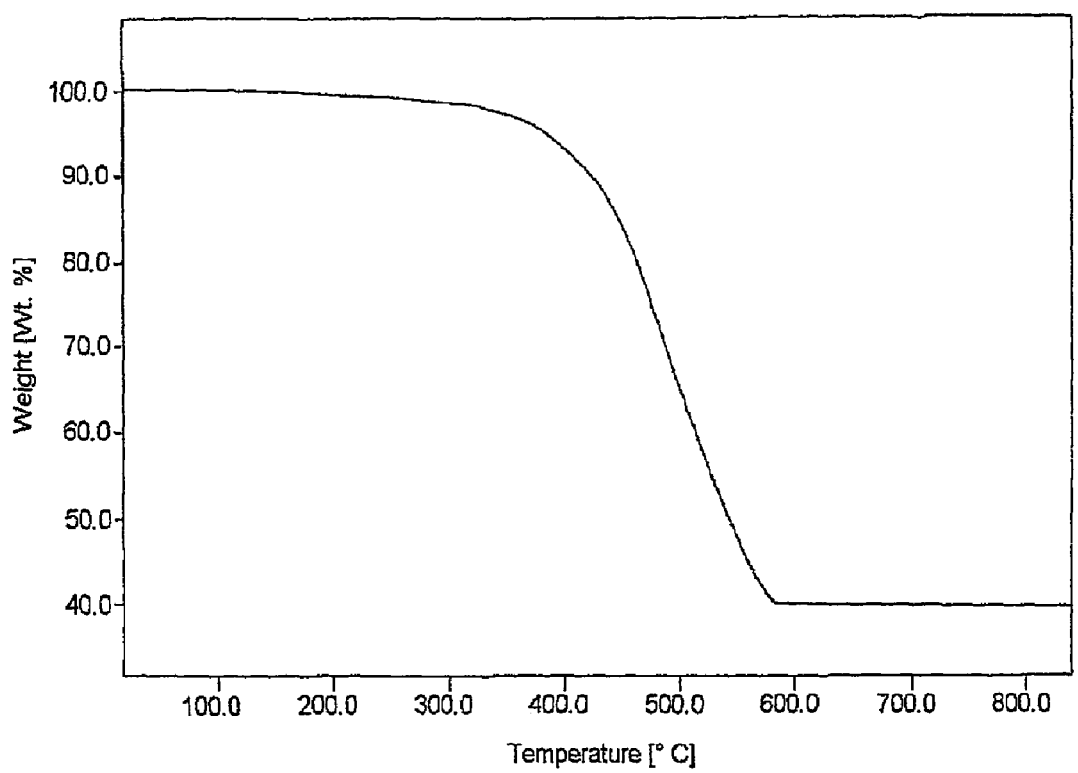

Figure 3. TGA curve of complex 15.
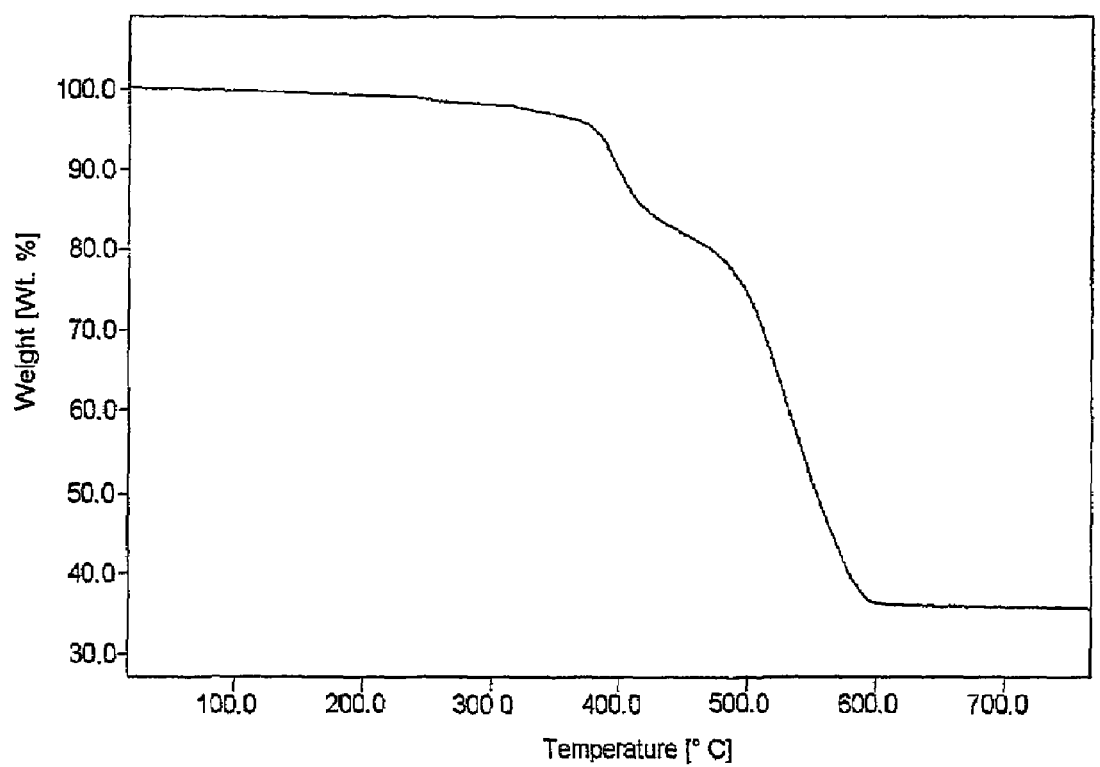

Figure 4. UV-vis absorption and emission spectra of complex 2 in dichloromethane at 298 K.
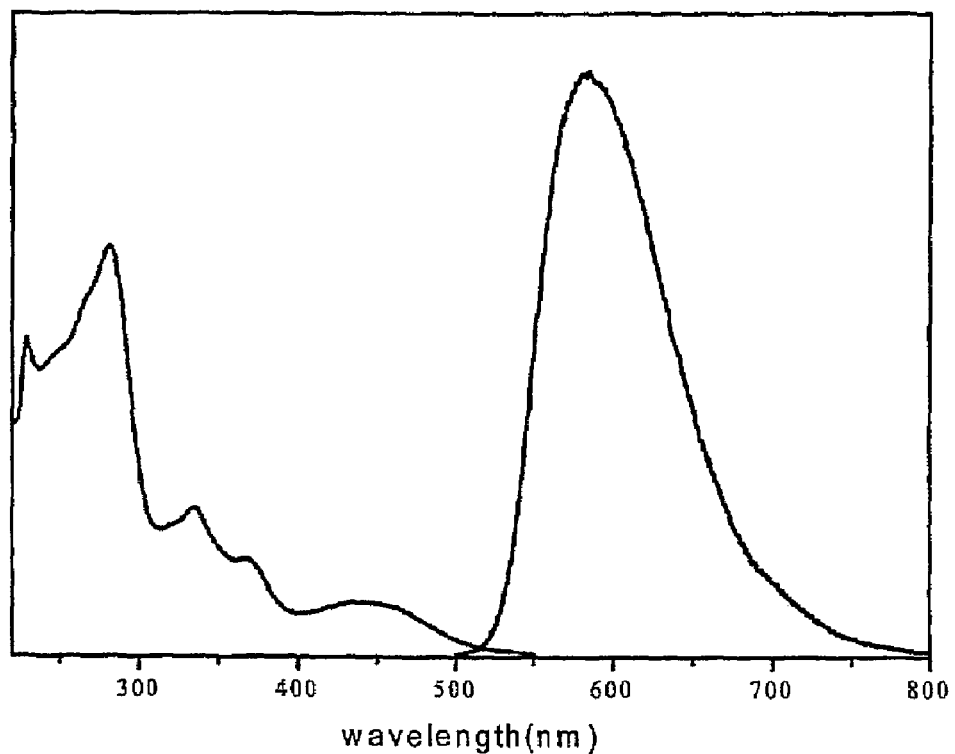

Figure 5. UV-vis absorption and emission spectra of complex 15 in dichloromethane at 298 K.
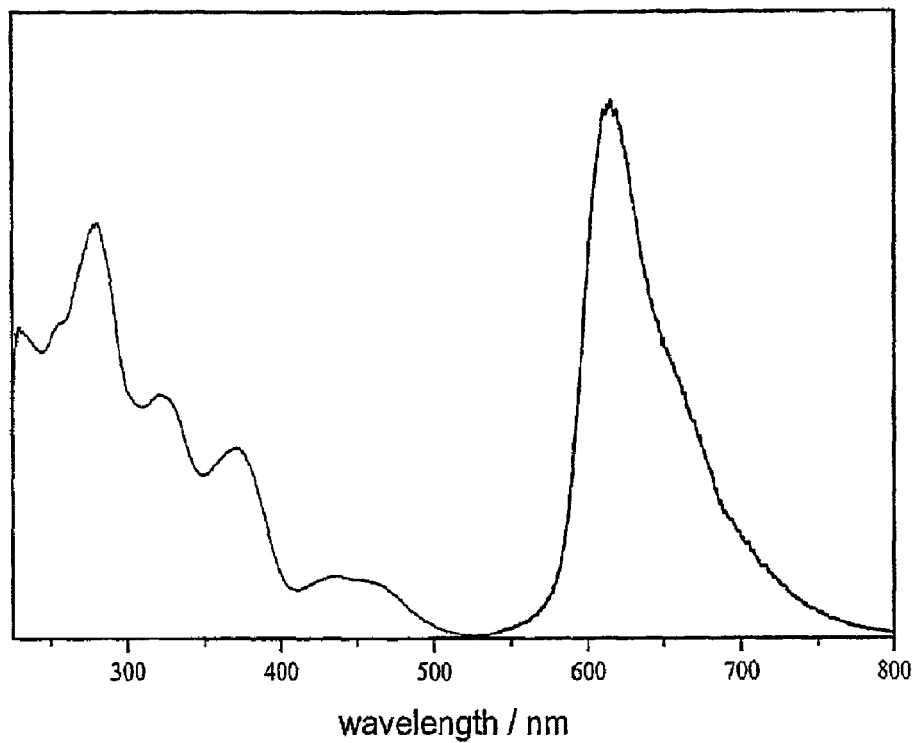

Figure 6. The heterostructure of OLEDs in present invention.
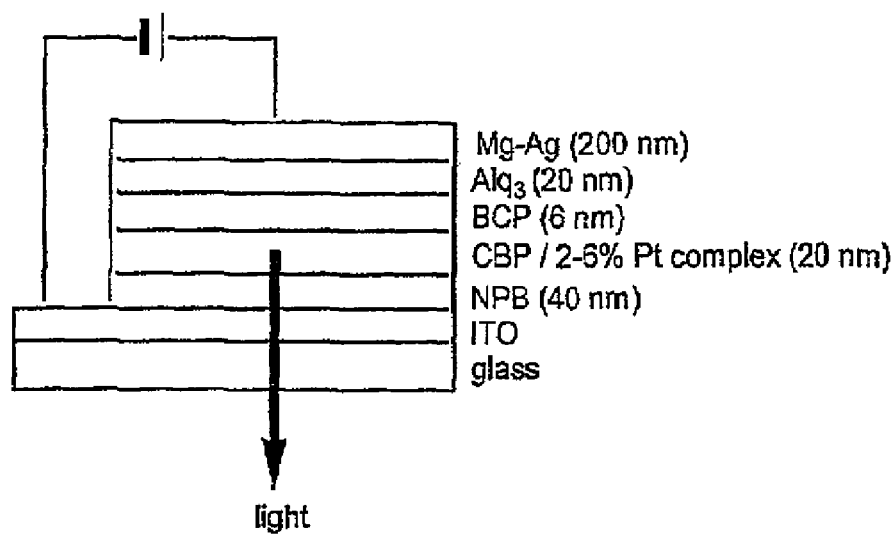

Figure 7. Electroluminescent spectrum, current-voltage (I-V) and luminance-voltage (B-V) curves and luminescent efficiency-current density curve of the device using complex 2 as emitter with a doping level of 2%.
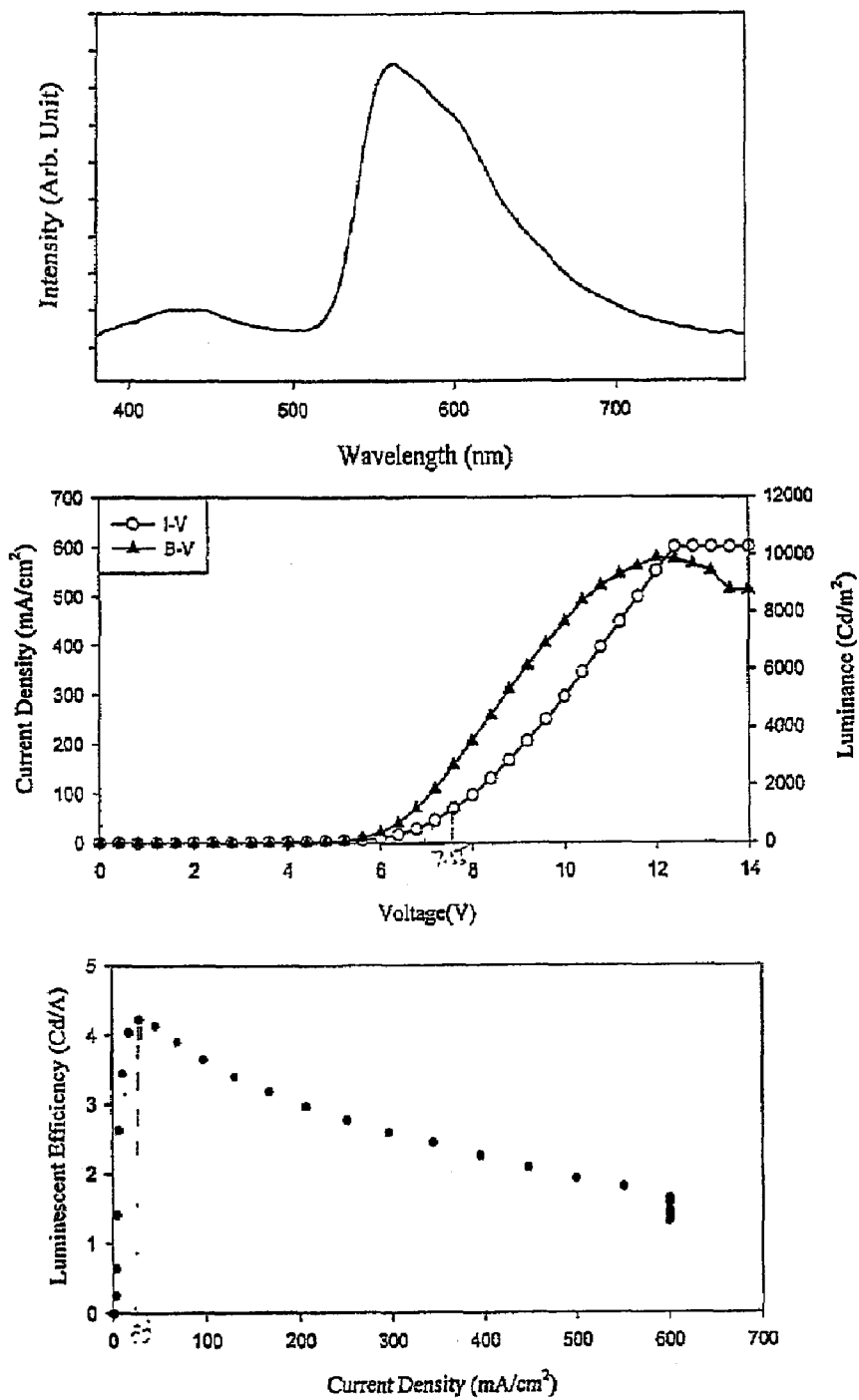

Figure 8. Electroluminescent spectrum, current-voltage (I-V) and luminance-voltage (B-V) curves and luminescent efficiency-current density curve of the device using complex 2 as emitter with a doping level of 4%.
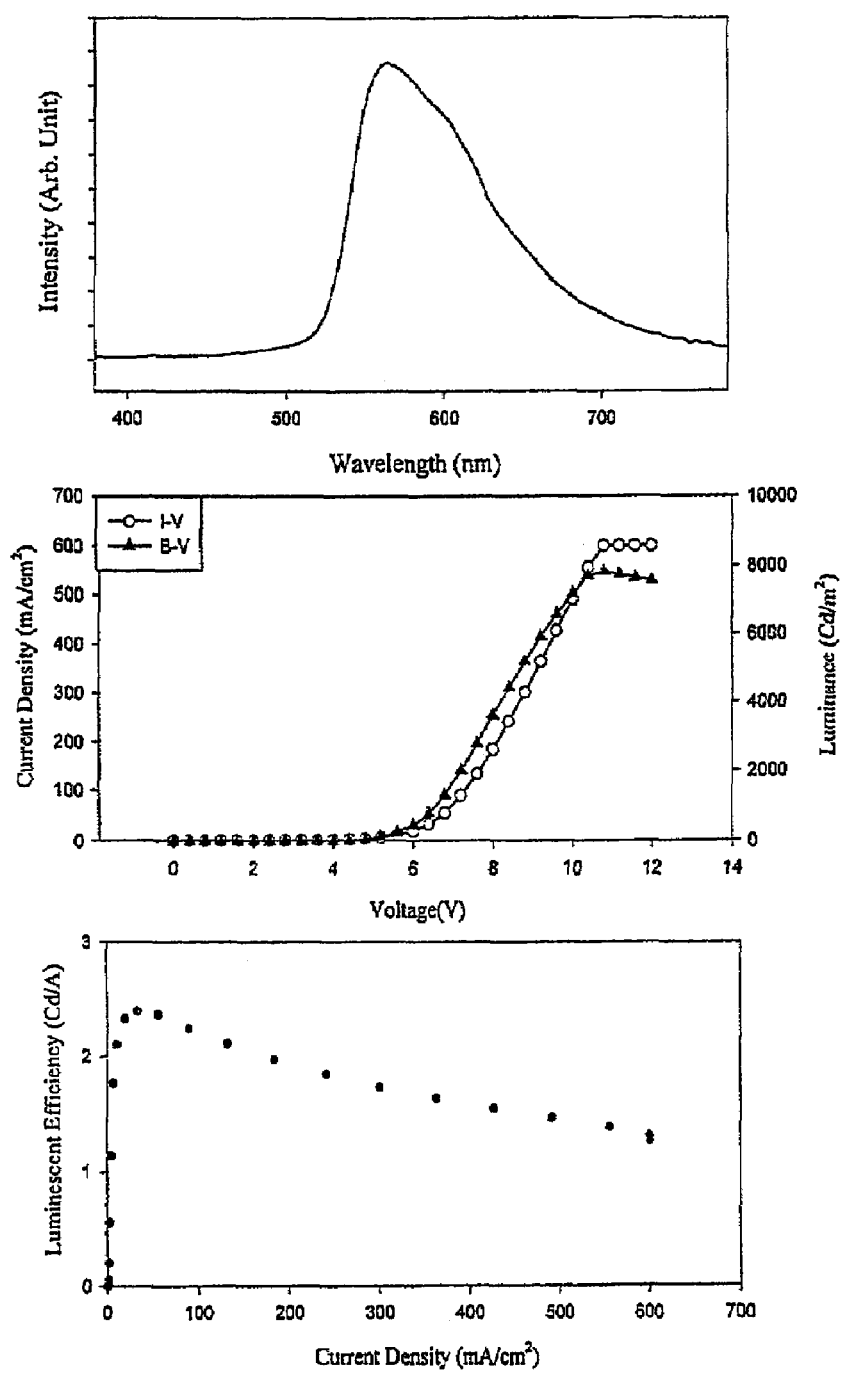

Figure 9. Electroluminescent spectrum, current-voltage (I-V) and luminance-voltage (B-V) curves and luminescent efficiency-current density curve of the device using complex 3 as emitter with a doping level of 4%.
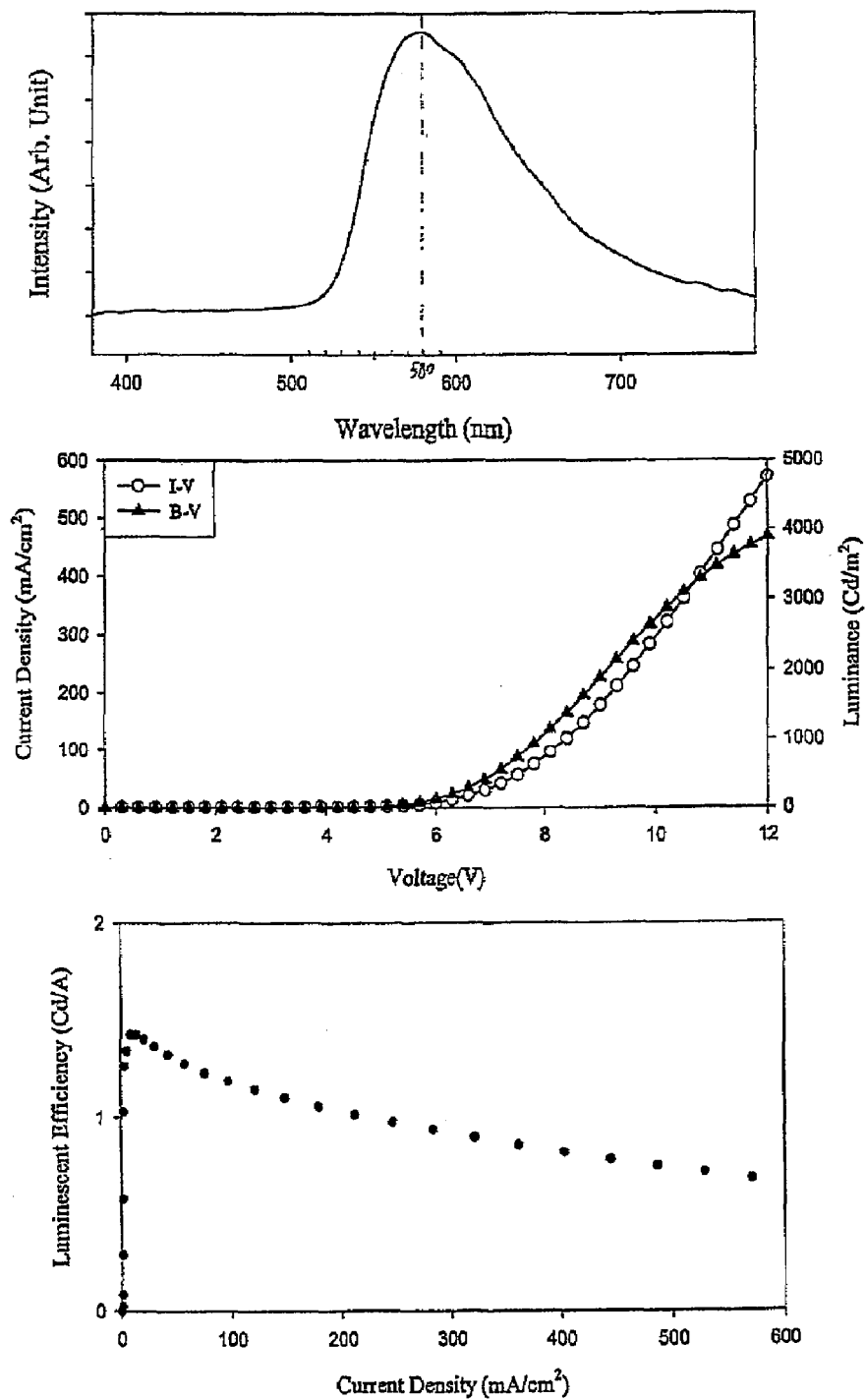

Figure 10. Electroluminescent spectrum, current-voltage (I-V) and luminance-voltage (B-V) curves and luminescent efficiency-current density curve of the device using complex 16 as emitter with a doping level of 4%.
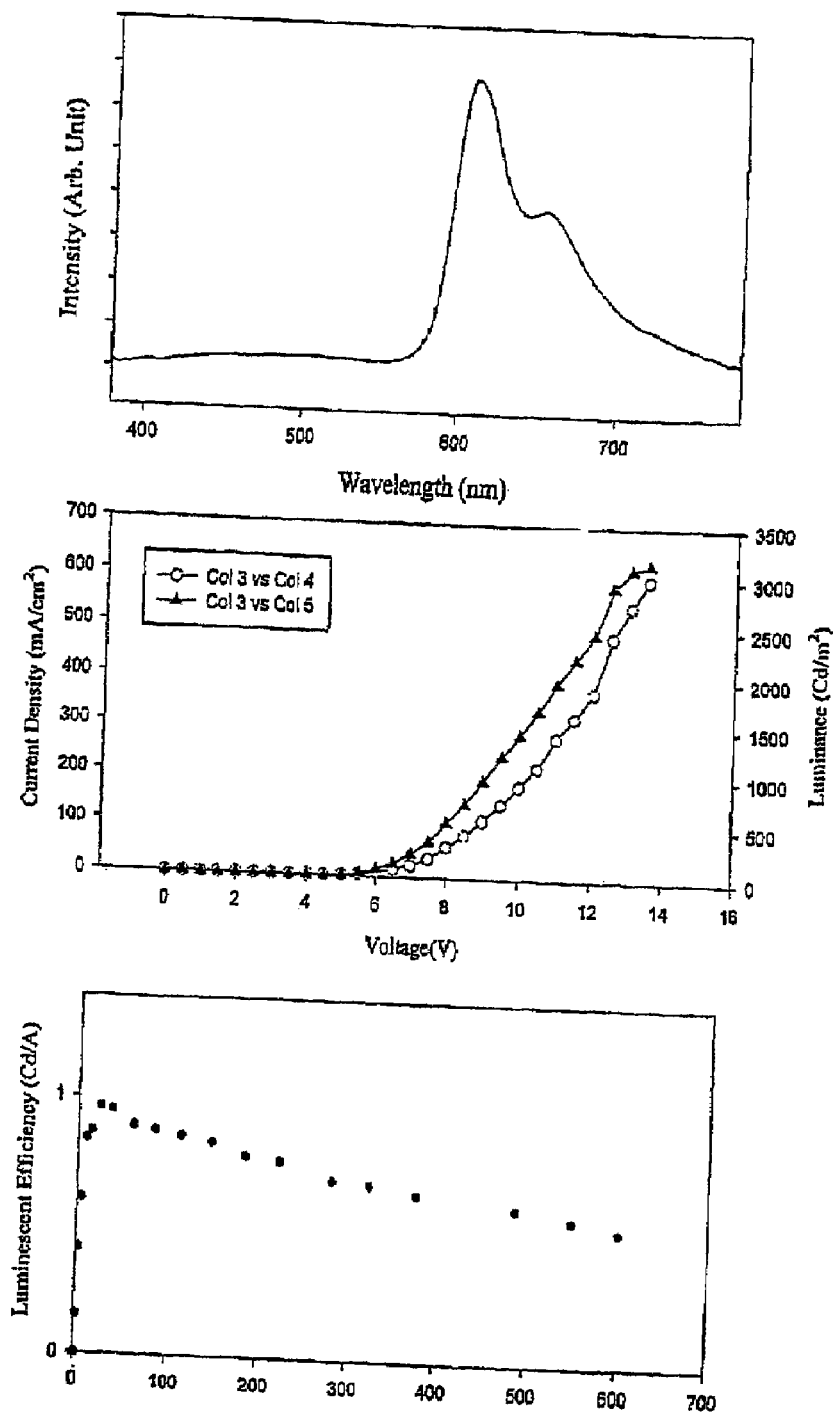

ORGANOMETALLIC LIGHT-EMITTING MATERIAL

RELATED APPLICATIONS

The present application is a continuation of U.S. application Ser. No. 11/468,757 titled "Organometallic Light-Emifting Material", filed on Aug. 30, 2006 by Che et al., which is a continuation of U.S. application Ser. No. 11/401,537 titled "Organometallic Light-Emitting Material", filed on Apr. 10, 2006 by Che et al., which is a continuation of to U.S. application Ser. No. 10/094,384 titled "Organometallic Light-Emitting Material", filed on Mar. 8, 2002 now U.S. Pat. No. 7,026,480 by Che et al., which claims priority to U.S. Provisional Patent Application Ser. No. 60/274,142, titled "Organometallic Light-Emitting Material", filed on Mar. 8, 2001, by Che et al.

FIELD OF THE INVENTION

This invention relates to light-emitting materials which are discrete organometallic molecules in nature, which can be deposited as a thin layer by vacuum deposition, and which can act as electrophosphorescent emitters in high-efficiency and high-brightness organic light-emitting devices (OLEDs).

BACKGROUND OF THE INVENTION

Tang and coworkers first reported on high-performance organic light-emitting devices (OLEDs) in 1987 (Tang, C. W.; et al. *Appl. Phys. Lett.* 51, 913 (1987)). Their discovery was based on employing a multilayer structure containing an emitting layer and a hole transport layer of a suitable organic substrate. $Alq_3$ (q=deprotonated 8-hydroxyquinolinyl) was chosen as the emitting material and proven to be of high-performance because (1) it can form uniform thin films under 1000 Å using vacuum deposition, (2) it is a good charge carrier and (3) it exhibits strong fluorescence. Since then, there has been a flourish of research on OLEDs and materials used in these devices. Indeed, nearly every large chemical company in the world with optoelectronic interests has demonstrated some level of interest in OLEDs. Clearly, OLED technology is heading directly and rapidly into the marketplace, as suggested in a commercial report by Stanford Resources (by David E. Mentley, "The Market Potential for Organic Light-Emitting Diode Displays," *Commercial Report*, available at http://www.stanfordresources.com). The attractiveness of OLEDs as it challenges traditional technologies such as cathode ray tubes (CRTs), liquid crystal displays (LCDs) and plasma displays is based on many features and advantages, including:

Low operating voltage,
Thin, monolithic structure,
Emits, rather than modulates light,
Good luminous efficiency,
Full color potential, and
High contrast and resolution.

OLED is a device built with organic semiconductors from which visible light can be emitted upon electrical stimulation, The basic heterostructure of an OLED is described in FIG. 1.

The layers may be formed by evaporation, spin-casting or chemical self-assembly. The thickness ranges from a few monolayers (self-assembled films) to about 1000 to 2000 Å. Such devices whose structure is based on the use of layers of organic optoelectronic materials generally rely on a common mechanism leading to optical emission, namely, the radiative recombination of a trapped charge. Under a DC bias, electrons are injected from a cathode (usually Ca, Al, Mg—Ag) and holes are injected from an anode (usually transparent indium tin oxide (ITO)) into the organic materials, where they travel in the applied field across the electron transporting layer (ETL) and the hole transporting layer (HTL) respectively until they meet, preferably on molecules in the emitting layer, and form a luminescent excited state (Frenkel exciton) which, under certain conditions, experiences radiative decay to give visible light. The electroluminescent material may be present in a separate emitting layer between the ETL and the HTL in what is referred as a multi-layer heterostructure. In some cases, buffer layers and/or other functional layers are also incorporated to improve the performance of the device. Alternatively, those OLEDs in which the electroluminescent emitters are the same materials that function either as the ETL or HTL are referred to as single-layer heterostructures.

In addition to emissive materials that are present as the predominant component in the charge carrier layers (HTL or ETL), other efficient luminescent material(s) may be present in relatively low concentrations as a dopant in these layers to realize color tuning and efficiency improvement. Whenever a dopant is present, the predominant material in the charge carrier layer may be referred to as a host. Ideally, materials that are present as hosts and dopant are matched so as to have a high level of energy transfer from the host to the dopant, and to yield emission with a relatively narrow band centered near selected spectral region with high-efficiency and high-brightness.

While fluorescent emitters with high luminescence efficiencies have been extensively applied as dopant in OLEDs, phosphorescent emitters have been neglected in this domain. However, the quantum efficiency of an electrofluorescence device is limited by the low theoretical ratio of singlet exciton (25%) compared to triplet exciton (75%) upon electron-hole recombination from electrical excitation. In contrast, when phosphorescent emitters are employed, the potentially high energy/electron transfer from the hosts to the phosphorescent emitters may result in significantly superior electroluminescent efficiency (Baldo, M. A.; et al. *Nature* 395, 151(1998) and Ma, Y. G.; et al. *Synth. Met.* 94, 245 (1998)). Several phosphorescent OLED systems have been fabricated and have indeed proven to be of relative high-efficiency and high-brightness.

It is desirable for OLEDs to be fabricated using materials that provide electrophosphorescent emission corresponding to one of the three primary colors, ie., red, green and blue so that they may be used as a component layer in full-color display devices. It is also desirable that such materials are capable of being deposited as thin films using vacuum deposition techniques, which has been prove to be a common method for high-performance OLED fabrication, so that the thickness of the emitting layer can be precisely controlled.

Presently, the highest efficiencies and brightness have been obtained with green electrophosphorescent devices (15.4±0.2% for external quantum efficiency and almost 100% for internal efficiency, $10^5$ $Cd/m^2$ for maximum luminance) using $Ir(ppy)_3$ (ppy=deprotonated 2-phenylpyridine) as emitter (Adachi, C.; et al. *Appl. Pays. Lett.* 77, 904 (2000)). An OLED emitting saturated red light based on the electrophosphorescent dopant Pt(OEP) ($H_2OEP$=octaethylporphyrin) has also been published and patented (Burrows, P.; et al. U.S. Pat. No. 6,048,630) but the maximum luminance is only around 500 Cd $m^{-2}$. A relevant patent is the use of the cyclometalated platinum(II) complex $Pt(thpy)_2$ (thpy= deprotonated 2-(2-thioenyl)pyridine) as dopant and PVK (poly(N-vinyl)carbazole) as host in a orange OLED (Lamansky, S.; et al. WO Pat. No. 00/57676). However, the Pt(II) complex used by the inventors was not stable for sublimation or vacuum deposition, thus a spin-casting method was applied, which led to higher driving voltages, quantum efficiency of 0.11% and luminance of 100 Cd/m² were obtained at 22 V.

SUMMARY OF THE INVENTION

The present invention is directed to novel organometallic light-emitting materials which may be used as electrophosphorescent emitters or dopants in high-performance OLEDs. In particular, the present invention is directed to the design, synthesis, properties and applications of a family of phosphorescent emitters which, when added in effective amounts to suitable host material, including emissive compounds, electron transporting compounds and hole transporting compounds, tune the color of emission in the near-red range and enhance the device efficiency and brightness. Furthermore, the thermal stability of these phosphorescent emitters in the present invention are sufficient to allow sublimation, so that they may be readily incorporated into devices using vacuum deposition techniques, and hence high-performance electrophosphorescent devices prepared entirely from vacuum-deposited materials may be realized.

The family of electrophosphorescent emitters for use in the present invention are acetylide (alkynyl) complexes of the Group 10 metals, including platinum, with chemical structures of either Formula I or II:

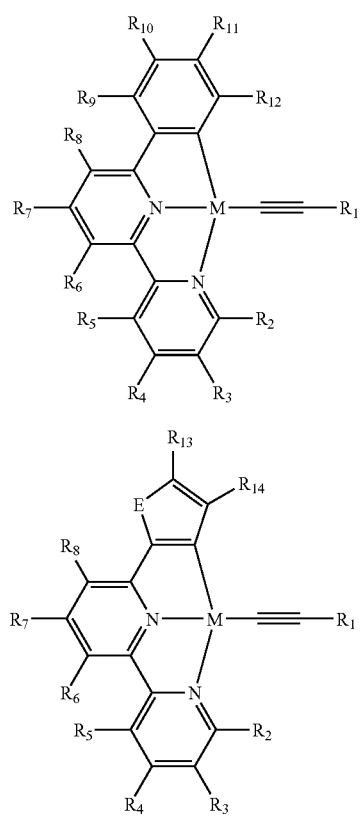

wherein E=Group 16 elements (including sulphur); M=Group 10 metal (including platinum); $R_1$-$R_{14}$ are each independently selected from the group consisting of hydrogen; halogen; alkyl; substituted alkyl; aryl; substituted aryl, with substituents selected from the group consisting of halogen, lower alkyl and recognized donor and acceptor groups. $R_1$, can also be selected from $(C{\equiv}C)_n R_{15}$, where $(C{\equiv}C)$ represents a carbon-carbon triple bond (acetylide group), n is selected from 1 to 10, and $R_{15}$ is selected from alkyl, aryl, substituted aryl, and tri(alkyl)silyl. Group 16 elements are also known as the Group VIA elements. Group 10 elements also belong to Group VIIIB.

As established by thermogravimetric analysis, some of these complexes are thermally stable up to ~400° C. These complexes are good phosphorescent emitters and give strong orange to red emissions ($\lambda_{max}$ 550-630 nm) in fluid solutions by photo excitation and in OLEDs by electrical stimulation.

Generally, the present invention is directed to the syntheses and OLED applications of the family of electrophosphorescent emitters defined by Formula I and II. Our claims include the synthetic method for these novel complexes as well as their use as light-emitting material. These OLED applications include OLEDs wherein these complexes are incorporated as components either by vacuum deposition, spin-casting or other device fabrication methods.

In the present invention, the light-emitting material for use as an emitter or dopant in an OLED can comprise one or more metal-acetylide (metal-alkynyl) groups. In alternative, the light-emitting material for use as an emitter or dopant in an OLED comprises one or more platinum-acetylide (platinum-alkenyl) groups. In one embodiment, the light-emitting material for use as an emitter or dopant in an OLED can comprises a platinum atom coordinated by a tridentate ligand using one carbon and two nitrogen atoms. In another embodiment, the light-emitting material for use as an emitter or dopant in an OLED comprising a platinum atom coordinated by a tridentate ligand bearing a deprotonated phenyl carbanion and 2,2'-bipyridine.

In an exemplary embodiment, the light-emitting material for use as an emitter or dopant in an OLED can have a chemical structure represented by either Formula I or II:

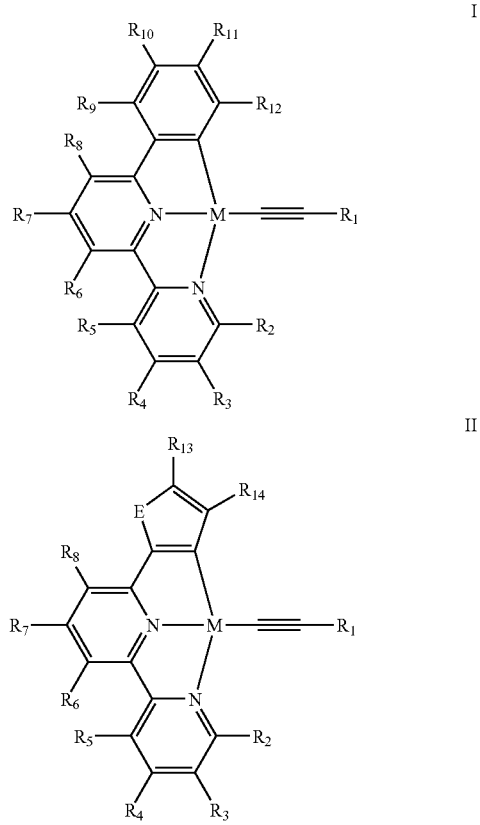

wherein E=Group 16 elements (including sulphur); M=Group 10 metal (including platinum); $R_1$-$R_{14}$ are each independently selected from the group consisting of hydrogen; halogen; alkyl; substituted alkyl; aryl; substituted aryl, with substituents selected from the group consisting of halogen, lower alkyl and recognized donor and acceptor groups. $R_1$ can also be selected from (C≡C)$_n$$R_{15}$, where (C≡C) represents a carbon-carbon triple bond (acetylide group), n is selected from 1 to 10, and $R_{15}$ is selected from alkyl, aryl, substituted aryl, and tri(alkyl)silyl.

in one embodiment, the light-emitting material can be deposited as a thin layer by sublimation or vacuum deposition. In another embodiment, the light-emitting material can be fabricated into OLEDs using spin-coating or other methods.

BRIEF DESCRIPTION OF THE FIGURES

FIG. 1. General heterostructure of OLEDs.
FIG. 2. TGA curve of complex 2.
FIG. 3. TGA curve of complex 15.
FIG. 4. UV-vis absorption and emission spectra of complex 2 in $CH_2Cl_2$ at 298 K.
FIG. 5. UV-vis absorption and emission spectra of complex 15 in $CH_2Cl_2$ at 298 K.
FIG. 6. The heterostructure of OLEDs in present invention.
FIG. 7. Electroluminescent spectrum, current-voltage (I-V) and luminance-voltage (B-V) curves and luminescent efficiency-current density curve of the device using complex 2 as emitter with a doping level of 2%.
FIG. 8. Electroluminescent spectrum, current-voltage (I-V) and luminance-voltage (B-V) curves and luminescent efficiency-current density curve of the device using complex 2 as emitter with a doping level of 4%.
FIG. 9. Electroluminescent spectrum, current-voltage (I-V) and luminance-voltage (B-V) curves and luminescent efficiency-current density curve of the device using complex 3 as emitter with a doping level of 4%.
FIG. 10. Electroluminescent spectrum, current-voltage (I-V) and luminance-voltage (B-V) curves and luminescent efficiency-current density curve of the device using complex 16 as emitter with a doping level of 4%.

DETAILED DESCRIPTION OF THE INVENTION

The present invention is generally directed to syntheses and properties of a family of organometallic light-emitting materials and their applications in high-performance OLEDs. These novel complexes possess several chemical and structural characteristics as follows:

Cyclometalated diimine complexes of Group 10 metals, including platinum,
Neutral molecules,
Square planar coordination environment around metal,
Tridentate ligands defined as (C^N^N) occupy three of the coordination sites, and
Acetylide (alkynyl) group occupies the fourth coordination site.

The type of [(C^N^N)Pt(II)] complexes which-combine the structural and spectroscopic characteristics of both diimine and cyclometalated Pt(II) complexes have been reported ((a) Lai, S. W.; et al. *Inorg. Chem.* 38, 4046 (1999). (b) Cheung, T. C.; et al. *J. Chem. Soc., Dalton Trans.* 1645 (1996). (c) Lai, S. W.; et al. *Organometallics* 18, 3327 (1999). (d) Yip, J. H. K.; et al. *Inorg. Chem.* 39, 3537 (2000). (e) Neve, F.; et al. *Inorg. Chem.* 36, 6150 (1997)). The results demonstrated that these complexes are good room-temperature phosphorescent emitters both in solid state and in fluid solution. The relatively long-lived emissions occurring in the range of $\lambda_{max}$ 530-800 nun have been assigned to triplet metal-to-ligand charge transfer ($^3$MLCT) or metal-metal-to-ligand charge transfer ($^3$MMLCT) excited states.

The present invention will now be described in detail for specific preferred embodiment of the invention, it being understood that these embodiments are intended only as illustrative examples and the invention is not to be limited thereto.

Syntheses of the Complexes

We have synthesized a number of the tridenitate cyclometalated Pt(II) arylacetylides

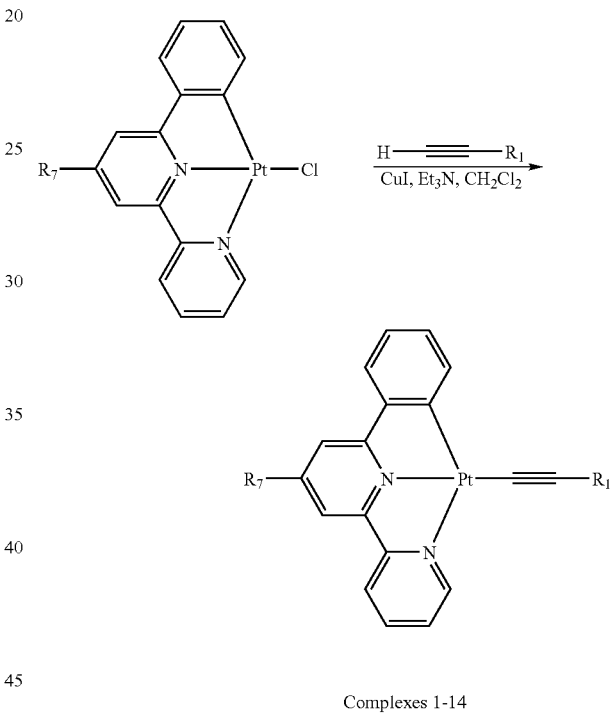

Complexes 1-14 with different substituents on the aryl rings which are depicted in either Formula I or II. The synthetic methods are shown in Scheme 1:

Scheme 1

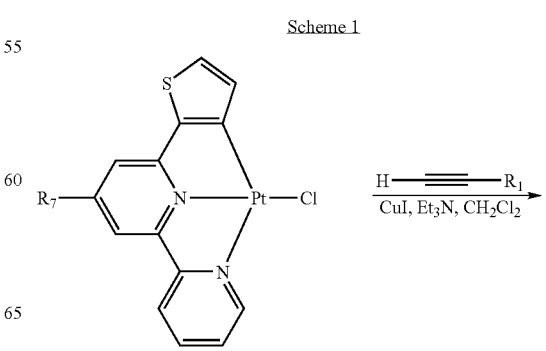

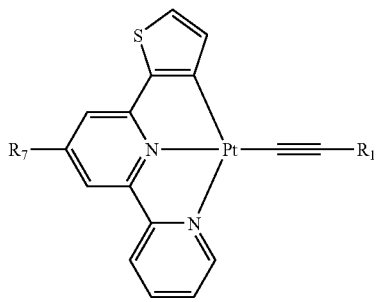

Complexes 15-16

The tridentate (C^N^N) ligands were prepared according to Kröhnke's method (Kröhnke, F. *Synthesis* 1 (1976)). The various acetylenes were prepared with Sonogashira's method (Takahashi, S. et al. *Synthesis* 627 (1980)). The Cl-ligated precursors [(C^N^N)PtCl] were prepared under Constable's condition (Constable, E. C.; et al. *J. Chem. Soc., Dalton Trans.* 2251 (1992) and 443 (1990)). The desired complexes were synthesized by Cu(I)-organic amine-catalyzed reactions. For example, to a mixture of [(C^N^N)PtCl] (0.33 mmol), terminal acetylene (1 mmol) and $Et_3N$ (3 mL) in degassed $CH_2Cl_2$ (30 mL) solution was added CuI (5 mg). The suspension was stirred for 12 h under a nitrogen atmosphere at room temperature and in the absence of light. The resultant mixture was rotatory-evaporated to dryness. The crude product was purified by flash chromatography (neutral $Al_2O_3$, $CH_2Cl_2$ as eluent) and/or recrystallization from dichloromethane/diethyl ether. Examples are listed in Table I but not limited by them:

TABLE I

| Complex | Chemical Structure | Characterization Data |
|---|---|---|
| 1 | (structure: Pt complex with −C≡C−SiMe$_3$) | orange crystalline powder. FAB MS: 524 ($M^+$ + H), 523 ($M^+$); $^1$H NMR (300 MHz, CDCl$_3$, 22° C., TMS): δ = 9.02(d, 1H, J=5.3 Hz), 7.94(t, 1H, J=7.8 Hz), 7.87(d, 1H, J=7.4 Hz), 7.82 (d, 1H, J=8.0 Hz), 7.68(t, 1H, J=8.0 Hz), 7.51(d, 1H, J=7.7 Hz), 7.45(t, 1H, J=7.5 Hz), 7.41(d, 1H, J=8.1 Hz), 7.21(d, 1H, J=7.2 Hz), 7.15(t, 1H, J=7.4 Hz), 7.02(t, 1H, J=7.5 Hz), 0.27(s, 9H). |
| 2 | (structure: Pt complex with −C≡C−phenyl) | orange crystalline powder. FAB MS: 528 ($M^+$ + H), 527 ($M^+$); $^1$H NMR (300 MHz, CDCl$_3$, 22° C., TMS): δ 9.15 (d, 1H, J=4.3 Hz), 7.97(m, 2H), 7.85(d, 1H, J=8.1 Hz), 7.75(t, 1H, J=8.0 Hz), 7.55(m, 8H), 7.48(m, 2H), 7.31(m, 3H), 7.17(t, 2H, J=7.0 Hz), 7.05(t, 1H, J=7.4 Hz) |
| 3 | (structure: Pt complex with −C≡C−C$_6$H$_4$−CH$_3$) | orange-red crystalline powder. FAB MS: 542 ($M^+$ + H), 541 ($M^+$); $^1$H NMR (300 MHz, CDCl$_3$, 22° C., TMS): δ = 9.07(d, 1H, J=4.3 Hz), 7.92(m, 2H), 7.82(d, 1H, J=7.8 Hz), 7.69(t, 1H, J=8.0 Hz), 7.53(d, 1H, J=7.3 Hz), 7.43(m, 4H), 7.27(d, 1H, J=6.3 Hz), 7.15(t, 1H, J=7.3 Hz), 7.10(d, 2H, J=7.9 Hz), 7.02(t, 1H, J=7.5 Hz), 2.35(s, 3H). |

TABLE I-continued

| Complex | Chemical Structure | Characterization Data |
|---|---|---|
| 4 | [Pt(terpy)(C≡C-C6H4-OCH3)] | red crystalline powder. FAB MS: 558 (M+ + H), 557 (M+); $^1$H NMR (300 MHz, CDCl$_3$, 22° C., TMS): δ = 9.12(d, 1H, J=5.2 Hz), 7.95(m, 2H), 7.83(d, 1H, J=7.9 Hz), 7.72(t, 1H, J=8.0 Hz), 7.50(m, 3H), 7.49(d, 2H, J=8.8 Hz), 7.30(d, 1H, J=6.6 Hz), 7.16(t, 1H, J=7.4 Hz), 7.03(t, 2H, J=7.4 Hz), 6.84(d, 2H, J=8.8 Hz), 3.82(s, 3H). |
| 5 | [Pt(terpy)(C≡C-C6H4-Cl)] | orange-red crystalline powder. FAB MS: 562 (M+); $^1$H NMR (300 MHz, CDCl$_3$, 22° C., TMS): δ = 9.05(d, 1H, J=5.1 Hz), 7.94(t, 1H, J=7.8 Hz), 7.87(d, 1H, J=7.5 Hz), 7.81(d, 1H, J=7.9 Hz), 7.71(t, 1H, J=8.0 Hz), 7.52(d, 1H, J=7.7 Hz), 7.46(m, 2H), 7.45(d, 1H, J=8.5 Hz), 7.27(d, 1H, J=4.2 Hz), 7.23(d, 2H, J=8.8 Hz), 7.15(t, 1H, J=7.4 Hz), 7.03(t, 1H, J=7.4 Hz). |
| 6 | [Pt(terpy)(C≡C-C6H4-F)] | black-red crystals. FAB MS: 546 (M+ + H), 545(M+); $^1$H NMR (300 MHz, CDCl$_3$, 22° C., TMS): δ = 9.12(d, 1H, J=5.2 Hz), 7.97(t, 1H, J=7.9 Hz), 7.92(d, 1H, J=7.6 Hz), 7.84(d, 1H, J=8.0 Hz), 7.74(t, 1H, J=8.0 Hz), 7.56-7.47(m, 5H), 7.32(d, 1H, J=7.6 Hz), 7.17(t, 1H, J=7.4 Hz), 7.05(t, 1H, J=7.5 Hz), 6.98(pseudo-t, 2H, J=7.7 Hz). |
| 7 | [Pt(terpy)(C≡C-C6H4-NO2)] | orange crystalline powder. FAB MS: 573 (M+ + H), 572(M+); $^1$H NMR (300 MHz, d$_6$-DMSO, 22° C., TMS): δ = 8.98(d, 1H, J=4.5 Hz), 8.48(d, 1H, J=8.0 Hz), 8.32(t, 1H, J=8.0 Hz), 8.20(d, m1H, J=7.4 Hz), 8.14(d, 2H, J=8.8 Hz), 8.11(t, 1H, J=8.0 Hz), 7.99(d, 1H, J=7.8 Hz), 7.83(t, 1H, J=7.5 Hz), 7.68(d, 1H, J=7.3 Hz), 7.62(d, 1H, J=7.4 Hz), 7.58(d, 2H, J=8.9 Hz), 7.11(t, 1H, J=7.3 Hz), 7.05(t, 1H, J=7.3 Hz). |
| 8 | [Pt(terpy)(C≡C-thienyl)] | brown crystals. FAB MS: 534 (M+ + H), 533(M+); $^1$H NMR (300 MHz, d$_6$-DMSO, 22° C., TMS): δ = 8.94(d, 1H, J=5.1 Hz), 8.46(d, 1H, J=7.9 Hz), 8.30(t, 1H, J=7.8 Hz), 8.17(d, 1H, J=7.6 Hz), 8.08(t, 2H, J=7.9 Hz), 7.96(d, 1H, J=7.9 Hz), 7.84(t, 1H, J=6.4 Hz), 7.66(d, 1H, J=6.2 Hz), 7.59(d, 1H, J=7.4 Hz), 7.21(d, 1H, J=4.9 Hz), 7.10(t, 1H, J=7.3 Hz), 7.03(t, 1H, J=7.3 Hz), 6.97-6.92(m,2H). |

TABLE I-continued

| Complex | Chemical Structure | Characterization Data |
|---|---|---|
| 9 | 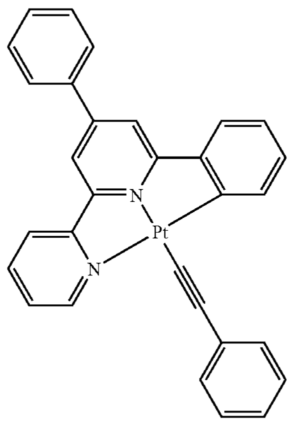 | orange crystalline powder. FAB MS: 604 (M+ + H), 603(M+); $^1$H NMR (300 MHz, d$_6$-DMSO, 22° C., TMS): δ = 8.99(d, 1H, J= 4.8 Hz), 8.68(d, 1H, J=8.0 Hz), 8.50(s, 1H), 8.32(t, 1H, J= 7.7 Hz), 8.24(s, 1H), 8.08-8.05(m, 2H), 7.84-7.78(m, 2H), 7.70(d, 1H, J=7.9 Hz), 7.61-7.55(m, 3H), 7.36(d, 1H, J= 7.2 Hz), 7.26(t, 1H, J=7.6 Hz), 7.17-7.01(m, 3H). |
| 10 | 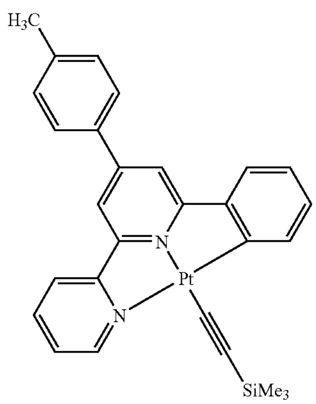 | orange crystalline powder. FAB MS: 614 (M+ + H), 613(M+); $^1$H NMR (300 MHz,, CDCl$_3$, 22° C., TMS): δ = 8.90(d, 1H, J= 5.4 Hz), 7.99(t, 1H, J=7.5 Hz), 7.90(d, 1H, J=8.0 Hz), 7.76 (d, 1H, J=6.2 Hz), 7.60-7.57(m, 3H), 7.40-7.31(m, 4H), 7.26 (d, 1H, J=6.1 Hz), 7.03-6.98(m, 2H), 2.48(s, 3H), 0.33(s, 9H). |
| 11 | 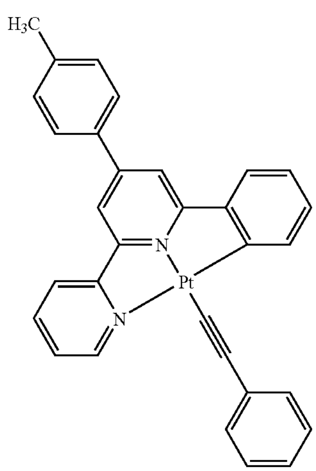 | orange crystalline powder. FAB MS: 618 (M+ + H), 617(M+); $^1$H NMR (300 MHz, d$_6$-DMSO, 22° C., TMS): δ = 9.04(d, 1H, J= 5.0 Hz), 8.69(d, 1H, J=7.9 Hz), 8.50(s, 1H), 8.34(t, 1H, J= 7.7 Hz), 8.24(s, 1H), 8.01(d, 2H, J=7.5 Hz), 7.84-7.74(m, 3H), 7.40-7.30(m, 4H), 7.30(t, 2H, J=7.5 Hz), 7.18-7.06(m, 3H), 2.40(s, 3H). |

TABLE I-continued

| Complex | Chemical Structure | Characterization Data |
|---|---|---|
| 12 | 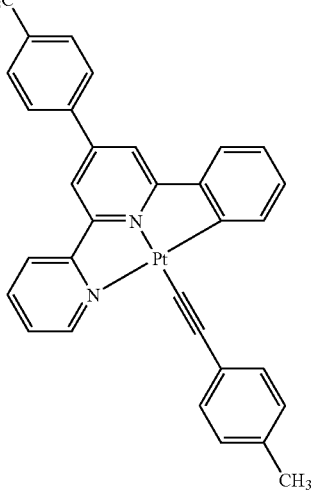 | red crystals. FAB MS: 632 (M$^+$ + H), 631 (M$^+$); $^1$H NMR (300 MHz, d$_6$-DMSO, 22° C., TMS): δ = 9.05(d, 1H, J=4.9 Hz), 8.56(d, 1H, J=8.0 Hz), 8.34(s, 1H), m8.20(t, 1H, J=7.9 Hz), 8.00(s, 1H), 7.85(d, 2H, J=8.1 Hz), 7.76-7.68(m, 2H), 7.62 (d, 1H, J=8.2 Hz), 7.31(d, 2H, J=8.1 Hz), 7.25(d, 2H, J= 8.0 Hz), 7.07-6.97(m, 4H), 2.39(s, 3H), 2.28(s, 3H). |
| 13 | 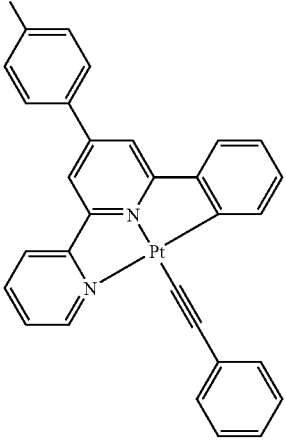 | orange crystalline powder. FAB MS: 634 (M$^+$ + H), 633(M$^+$); $^1$H NMR (300 MHz, d$_6$-DMSO, 22° C., TMS): δ = 9.00(d, 1H, J= 4.9 Hz), 8.69(d, 1H, J=8.1 Hz), 8.48(s, 1H), 8.32(t, 1H, J= 7.9 Hz), 8.26(s, 1H), 8.08(d, 2H, J=8.8 Hz), 8.06-7.81(m, 2H), 7.72(d, 1H, J=7.1 Hz), 7.35(d, 2H, J=7.1 Hz), 7.26(t, 2H, J=7.6 Hz), 7.16-7.04(m, 5H), 3.84(s, 3H). |
| 14 | 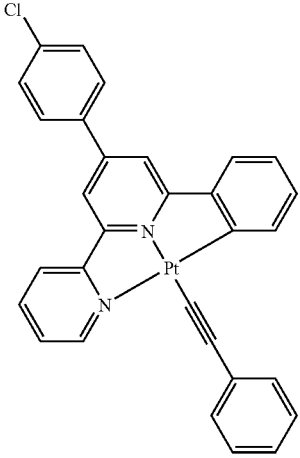 | brown crystalline powder. FAB MS: 638 (M$^+$); $^1$H NMR(300 MHz, d$_6$-DMSO, 22° C., TMS): δ = 8.99(broad, 1H), 8.64(d, 1H, J=7.7 Hz), 8.47(s, 1H), 8.31(t, 1H, J=7.6 Hz), 8.21(s, 1H), 8.09(d, 2H, J=8.1 Hz), 7.82-7.68(m, 3H), 7.62(d, 2H, J= 8.2 Hz), 7.38(d, 2H, J=7.2 Hz), 7.28(t, 2H, J=7.3 Hz), 7.18(t, 1H, J=7.0 Hz), 7.08-7.03(m, 2H). |

TABLE I-continued

| Complex | Chemical Structure | Characterization Data |
|---|---|---|
| 15 | 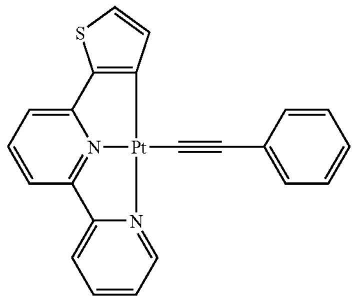 | brown needles. FAB MS: 534 (M⁺ + H), 533 (M⁺); $^1$H NMR (300 MHz, $d_6$-DMSO, 22° C., TMS): $\delta$ = 9.01(d, 1H, J=5.0 Hz), 8.46(d, 1H, J=8.2 Hz), 8.35(t, 1H, J=7.9 Hz), 8.02(d, 1H, J=7.6 Hz), 7.96(t, 1H, J=7.8 Hz), 7.85(t, 1H, J=6.4 Hz), 7.72(d, 1H, J=4.9 Hz), 7.56(d, 1H, J=7.3 Hz), 7.38(d, 2H, J=7.0 Hz), 7.29(t, 2H, J=7.6 Hz), 7.17(t, 1H, J=7.3 Hz), 7.11(d, 1H, J=4.6 Hz). |
| 16 | 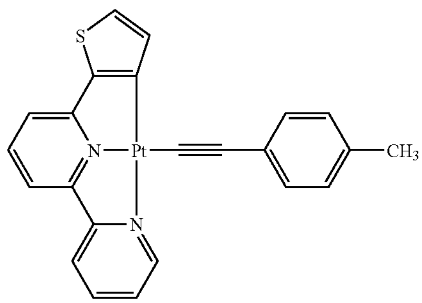 | brown needles. FAB MS: 548 (M⁺ + H), 547 (M⁺); $^1$H NMR (300 MHz, $d_6$-DMSO, 22° C., TMS): $\delta$ = 9.03(d, 1H, J=5.2 Hz), 8.47(d, 1H, J=8.2 Hz), 8.34(t, 1H, J=7.2 Hz), 8.02(d, 1H, J=7.9 Hz), 7.96(t, 1H, J=7.7 Hz), 7.86(t, 1H, J=6.3 Hz), 7.73(d, 1H, J=4.9 Hz), 7.56(d, 1H, J=7.6 Hz), 7.26(d, 2H, J=7.9 Hz), 7.13(d, J=4.6 Hz), 7.11(d, 2H, J=7.9 Hz), 2.30(s, 3H). |

Thermal-stability of the Complexes

Ideally, a low molecular weight component to be used in OLEDs should be sublimable and stable at standard deposition conditions. Importantly, many of the complexes in the present invention are thermally stable up to ~400° C. and decompose to give metallic platinum only at temperature above 420° C. (see TGA curves for complexes 2 and 15 in FIGS. 2 and 3 respectively).

The observed thermal stability of these complexes described in the present invention which contain a tridentate cyclometalating ligand, contrasts sharply with the bidentate Pt(thpy)$_2$ emitter described by Lamasky et al. which are unstable upon sublimation.

Spectroscopic Properties of the Complexes

In present invention, the ligation of an acetylide group to the (C^N^N)Pt(II) moiety neutralizes the positive charge centered on Pt(II), enhances the stability of these complexes, and moreover, shifts the $^3$MLCT emission bathochromically. The family of complexes depicted by Formula I and II display strong orange to red photoluminescence in fluid solution. Examples of characteristic absorption and emission band of these emitters in present invention are summarized in Table II:

Notice that all the data were collected with degassed $CH_2Cl_2$ solution at 298 K. Exemplified absorption and emission spectra for complexes 2 and 15 are shown in FIGS. 4 and 5 respectively. The intense orange to red phosphorescence of the complexes in the present invention together with their stability towards sublimation means that these materials can be used as emitters or dopants in high-performance OLEDs.

Organic Light-emitting Devices

The devices using the complexes in present invention, as fabricated by Prof. S. T. Lee of City University of Hong Kong, possess the multi-layer heterostructure shown in FIG. 6.

All the organic layers including the Pt complexes described above and cathodes were vacuum-deposited onto the ITO subtrate. NPB (N,N'-di-1-naphthyl-N,N'-diphenyl-benzidine) and Alq$_3$ (q=8-hydroxyquinolinyl) were used as the hole transporting and electron transporting layer, respectively. BCP (2,9-dimethyl-4,7-diphenyl-1,10-phenanthroline, bathocuproine) was used to confine excitons within the luminescent zone. Magnesium silver alloy was applied as the cathode. The selected Pt complex was doped into the conductive host material CBP (4,4'-N,N'-dicarbazole-biphenyl) as

TABLE II

| Complex (see Table I) | Absorption MLCT Band/nm ($\epsilon$/mol dm$^{-1}$ cm$^{-1}$) | Emission $\lambda_{max}$/nm ($\tau_0$/µs; $\phi_0$) |
|---|---|---|
| 1 | 427 (5490), 450 (sh, 4920), 505 (sh, 430) | 570 (0.31; 0.041) |
| 2 | 434 (5180), 455 (4940), 510 (sh, 470) | 582 (0.39; 0.037) |
| 3 | 440 (5090), 465 (sh, 4950), 515 (sh, 1190) | 600 (0.17; 0.019) |
| 4 | 440 (4200), 460 (sh, 4220), 520 (sh, 1570) | 630 |
| 5 | 432 (8670), 455 (sh, 8310), 515 (sh, 720) | 598 (0.53; 0.076) |
| 6 | 433 (4880), 453 (sh, 4760), 515 (sh, 640) | 585 (0.33; 0.033) |
| 7 | 415 (sh, 12930), 510 (sh, 540) | 560 (0.93; 0.077) |
| 15 | 436 (4970), 460 (sh, 4490), 515 (sh, 460) | 615 (1.02; 0.029), 660 (sh) |
| 16 | 442 (5010), 465 (sh, 4800), 520 (sh, 670) | 616 (0.91; 0.025), 660 (sh) | phosphorescent emitter. The optimal doping levels were adjusted at 2, 4 and 6% and electroluminescence from the Pt complexes were observed.

EXAMPLES

A number of examples are listed below to further illustrate the invention

Example 1

Complex 2 was used as the emitter. Typical electroluminescent spectrum, current-voltage (I-V) and luminance-voltage (B-V) curves and luminescent efficiency-current density curve of the device with a doping level of 2% are shown in FIG. 7. Turn-on voltage: ~5 V; maximum luminance: 9600 Cd/m$^2$ at 12 V; maximum efficiency: 4.2 Cd/A at 25 mA/cm$^2$. In the electroluminescent spectrum, a peak at 430 nm besides the band at 560-630 nm is observed, indicating insufficient energy transfer between the host and the dopant.

Example 2

The performance of the device using complex 2 as emitter with a doping level of 4% are shown in FIG. 8. Turn-on voltage: ~5 V; maximum luminance: 7900 Cd/m$^2$ at 10 V; maximum efficiency: 2.4 Cd/A at 30 mA/cm$^2$. At this doping level, energy transfer between the host and the dopant is saturated, thus emission from the host is avoided.

Example 3

Complex 3 was used as the emitter. The performance of the device with a doping level of 4% are shown in FIG. 9. A bathochromic electroluminescence is observed ($\lambda_{max}$ 580 nm), which is coinciding with the trend of the photoluminescence shown by these complexes in room-temperature CH$_2$Cl$_2$ solutions. Turn-on voltage: ~5 V; maximum luminance: 4000 Cd/m$^2$ at 12 V; maximum efficiency: 1.4 Cd/A at 20 mA/cm$^2$.

Example 4

Complex 16 was used as the emitter. The performance of the device with a doping level of 4% are shown in FIG. 10. The electroluminescence is red with vibronically structured emission spectrum ($\lambda_{max}$ 610 nm, 660 ni). Turn-on voltage: ~5 V; maximum luminance: 3200 Cd/m$^2$ at 13 V; maximum efficiency: 1.0 Cd/A at 30 mA/cm$^2$.

Generally, the organometallic light-emitting materials as depicted in FIGS. I and II in present invention are demonstrated to be novel electrophosphorescent emitters applicable to high-efficiency and -brightness orange to red light OLEDs.

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall vathin the true spirit and scope of the present invention.

A number of references have been cited and the entire disclosures of which are incorporated herein by reference.

What is claimed is:

1. A method comprising:
    doping a host material with an emissive material, the emissive material having an emission maximum in the near red range, wherein the emissive material comprises a tridentate ligand defined as (C^N^N) and an acetylide group coordinated to a group 10 metal; and
    disposing the doped host material between an electron transporting layer and a hole transporting layer in an OLED.

2. The method of claim 1, wherein the disposing comprises:
    disposing a hole transporting layer on an anode layer;
    disposing the doped host material on the hole transporting layer;
    disposing a bathocuproine buffer layer on the doped host material layer; and
    disposing an electron transporting layer on the bathocuproine layer.

3. The method according to claim 1 wherein the emissive material comprises one or more platinum-acetylide groups.

4. The method according to claim 1 wherein the emissive material comprises a platinum atom coordinated by a tridentate ligand comprising a deprotonated phenyl carbanion and 2,2'-bipyridine.

5. The method according to claim 2 wherein said disposing a bathocuproine buffer layer or said disposing an electron transporting layer, or combinations thereof, is carried out via vacuum deposition or spin-casting.

6. The method of claim 1, wherein the emissive material has an emission maximum between 550-630 nm.

7. The method of claim 1, wherein the group 10 metal is platinum.

8. The method of claim 1, wherein the emissive material is according to formula I or II,

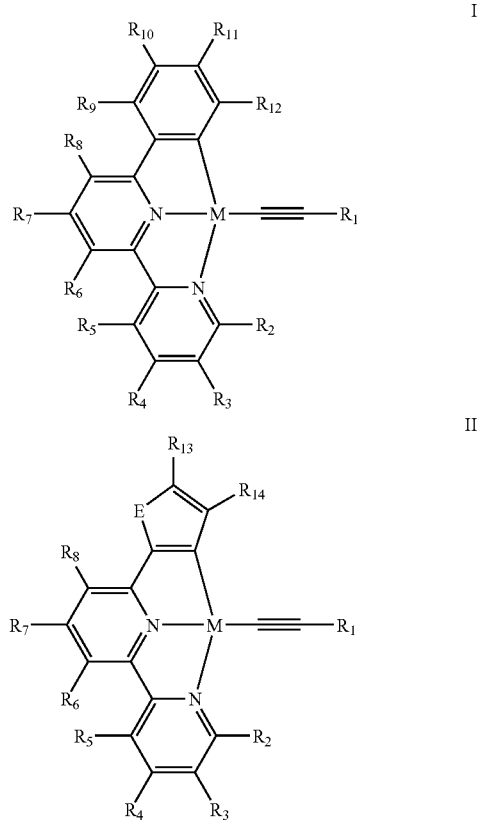

wherein:
    E is a Group 16 element;
    M is a Group 10 metal;

$R_1$ is selected from the group consisting of hydrogen, halogen, alkyl, substituted alkyl, aryl, and substituted aryl; or $R_1$ is $(C{\equiv}C)_n R_{15}$, wherein:

$(C{\equiv}C)$ is a carbon-carbon triple bond;

n is selected from 1 to 10; and $R_{15}$ is selected from alkyl, aryl, substituted aryl, and tri(alkyl)silyl;

and $R_2$-$R_{14}$ are each independently selected from the group consisting of hydrogen, halogen, alkyl, substituted alkyl, aryl, and substituted aryl.

9. The method of claim 1, wherein the emissive material is selected from the group consisting of,

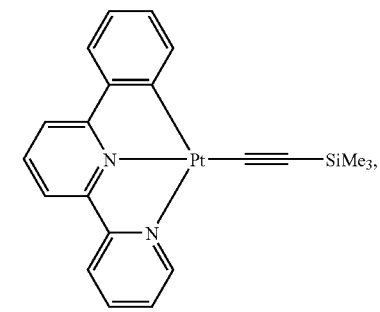

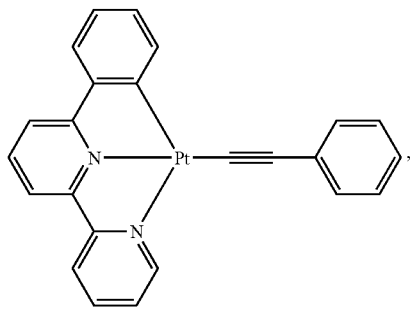

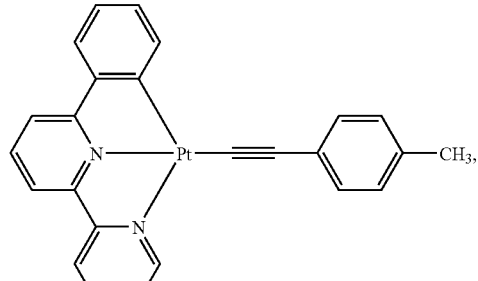

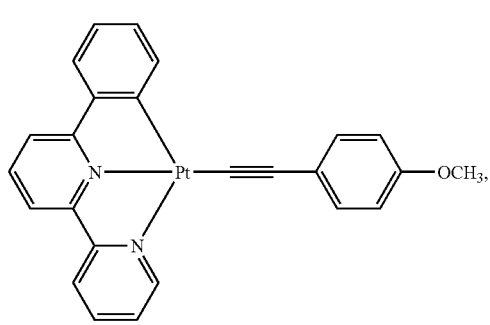

-continued

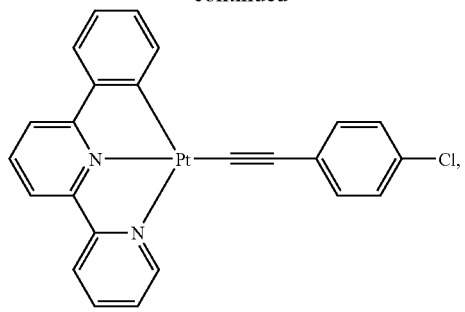

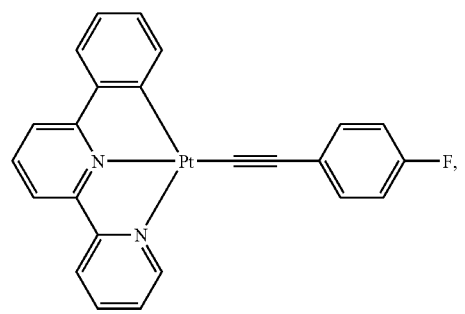

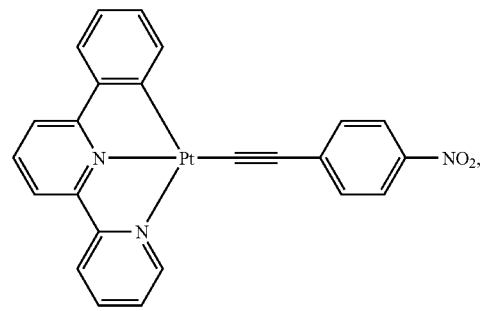

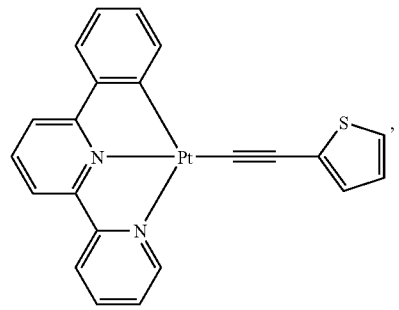

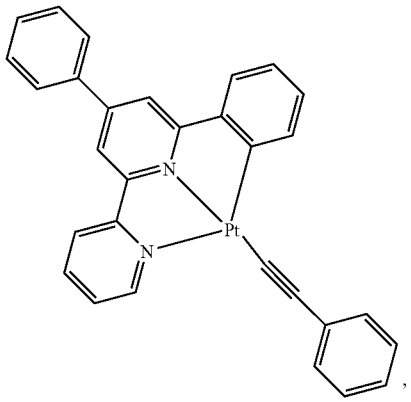

-continued

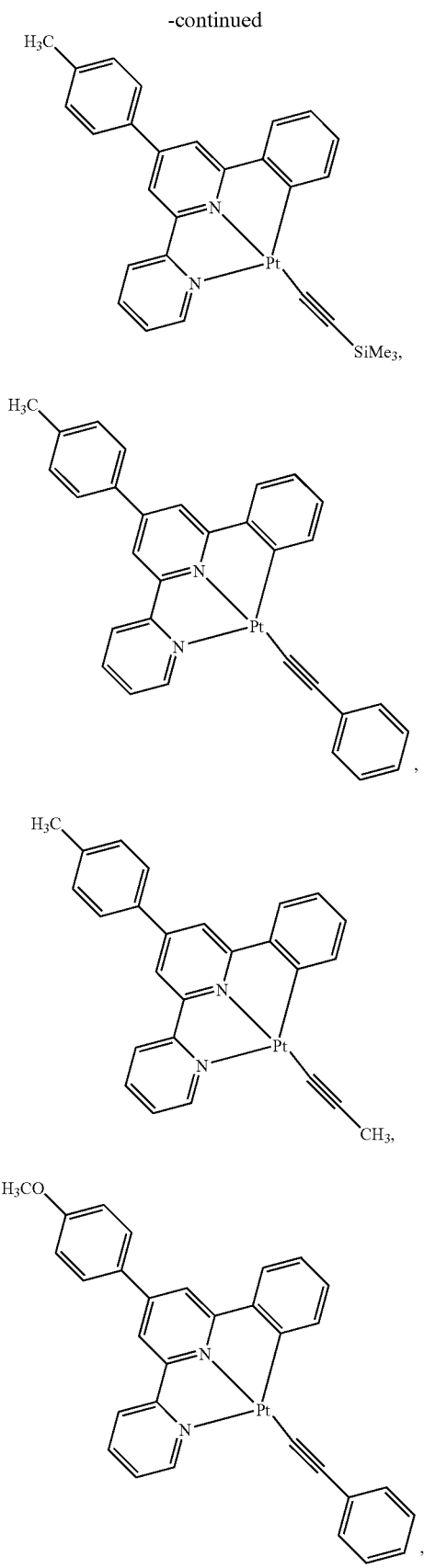

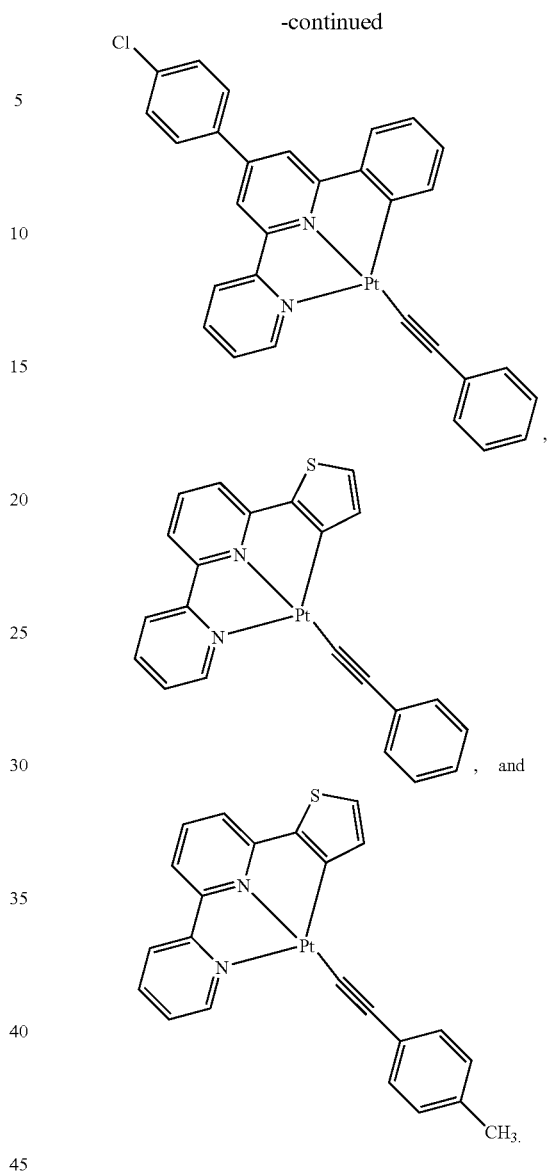

10. The method of claim 1, wherein the emissive material is thermally stable up to 400° C.

11. The method of claim 1, wherein the doped host material is disposed by sublimation or vacuum deposition.

12. The method of claim 1, wherein the doped host material is disposed by spin-casting.

13. The method of claim 1, wherein the electron transporting layer comprises tris(8-hydroxyquinoline)aluminum.

14. The method of claim 1, wherein the hole transporting layer comprises N,N'-di-1-naphthyl-N,N'-diphenylbenzidine.

15. The method of claim 1, wherein the host material comprises 4,4'-N,N'-dicarbazole-biphenyl.

16. The method of claim 2, wherein the hole transporting layer, the doped host material, the electron transporting layer, and the bathocuproine buffer layer are each disposed by vacuum deposition.

17. The method of claim 2, wherein the anode layer is a transparent ITO substrate.

* * * * *